United States Patent
Helmick

(10) Patent No.: US 10,201,567 B2
(45) Date of Patent: Feb. 12, 2019

(54) ARTICLE OF APPAREL FOR TOPICAL DELIVERY OF BIORESORBABLE MATERIAL

(71) Applicant: Under Armour, Inc., Baltimore, MD (US)

(72) Inventor: Amelia Helmick, Boston, MA (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 15/295,020

(22) Filed: Oct. 17, 2016

(65) Prior Publication Data

US 2017/0106015 A1   Apr. 20, 2017

Related U.S. Application Data

(60) Provisional application No. 62/241,868, filed on Oct. 15, 2015.

(51) Int. Cl.
| | |
|---|---|
| *A61K 33/06* | (2006.01) |
| *A61K 9/00* | (2006.01) |
| *A41B 1/08* | (2006.01) |
| *A41D 13/00* | (2006.01) |

(52) U.S. Cl.
CPC .......... *A61K 33/06* (2013.01); *A41B 1/08* (2013.01); *A41D 13/0015* (2013.01); *A61K 9/0014* (2013.01); *A41D 2400/32* (2013.01)

(58) Field of Classification Search
None
See application file for complete search history.

(56) References Cited

U.S. PATENT DOCUMENTS

| | | | |
|---|---|---|---|
| 4,517,893 A * | 5/1985 | Wile | B41F 15/12 101/123 |
| 8,048,150 B2 | 11/2011 | Weber et al. | |
| 2003/0054141 A1 * | 3/2003 | Worley | A41D 31/0038 428/195.1 |
| 2011/0318986 A1 * | 12/2011 | Pourdeyhimi | D04H 1/541 442/363 |
| 2014/0234394 A1 * | 8/2014 | McDonough | A61K 9/0014 424/444 |
| 2016/0076195 A1 * | 3/2016 | Ko | D06M 11/00 503/206 |
| 2016/0271073 A1 * | 9/2016 | Falken | C09D 11/106 |

FOREIGN PATENT DOCUMENTS

| | | | |
|---|---|---|---|
| WO | 1998002056 | 1/1998 | |
| WO | WO-2014185590 A1 * | 11/2014 | ........... D06M 11/00 |
| WO | WO2015171467 A1 | 11/2015 | |

* cited by examiner

*Primary Examiner* — Kevin S Orwig
*Assistant Examiner* — Barbara S Frazier
(74) *Attorney, Agent, or Firm* — Maginot, Moore & Beck LLP

(57) ABSTRACT

The present invention is directed toward an article of apparel configured to deliver a bioabsorbable alloy to the skin of a wearer. In an embodiment, the apparel is a textile base layer and a delivery layer oriented to contact the skin of the wearer. The delivery layer is formed from a composition including a magnesium alloy. In another embodiment, the textile is formed of strands coated with the magnesium alloy composition. In still further embodiments, the strands are formed of the alloy. The apparel may be configured to release a therapeutically effective amount to the user.

12 Claims, 8 Drawing Sheets

ARTICLE OF APPAREL FOR TOPICAL DELIVERY OF BIORESORBABLE MATERIAL

CROSS REFERENCE TO RELATED APPLICATIONS

The present application is a nonprovisional of U.S. provisional application No. 62/241,868, filed 15 Oct. 2015 and entitled "Article of Apparel for Topical Delivery of Bioresorbable Material," the disclosure of which is incorporated herein by reference in its entirety.

FIELD OF THE INVENTION

The present invention is directed to an article of apparel including a bioresorbable material and, in particular, an article of apparel adapted to deliver a magnesium alloy to the skin of the wearer for absorption into the body.

BACKGROUND OF THE INVENTION

Biomaterials are used in numerous medical applications today, such as fixation devices, replacements and surgical equipment. Implants are typical examples of a biomaterial application and there are several different implant materials used today. For example, magnesium is a biomaterial known for its therapeutic benefits. Magnesium is believed to contribute to the relaxation and contraction of muscles improving the rate of healing to the damaged site. Magnesium sulfate, for example, is often used to soothe soreness and reduce inflammation. Magnesium compounds may be applied topically, absorbing the compound in through the skin.

For athletes, magnesium is believed to be beneficial in regulating heart rhythm, reducing blood pressure, and in producing ATP. In light of the benefits of magnesium, it would be beneficial to provide athletic apparel capable of delivering magnesium topically to a wearer.

BRIEF SUMMARY OF THE INVENTION

The present invention is directed toward an article of apparel configured to deliver a bioresorbable material to the skin of a wearer. In an embodiment, the apparel is a textile base layer and a delivery layer oriented to contact the skin of the wearer. The delivery layer is formed from a composition including a bioresorbable alloy and, in particular, a magnesium alloy. In another embodiment, the textile is formed of strands coated with the alloy composition, or of strands extruded with the alloy. In another embodiment, fine wires composed of the alloy will be incorporated into the garment's knit or woven structure. With this configuration, the apparel may release a therapeutically effective amount of material (e.g., magnesium) to the wearer.

BRIEF DESCRIPTION OF THE SEVERAL VIEWS OF THE DRAWINGS

Like reference numerals have been used to identify like elements throughout this disclosure.

DETAILED DESCRIPTION OF THE INVENTION

Figure 1:
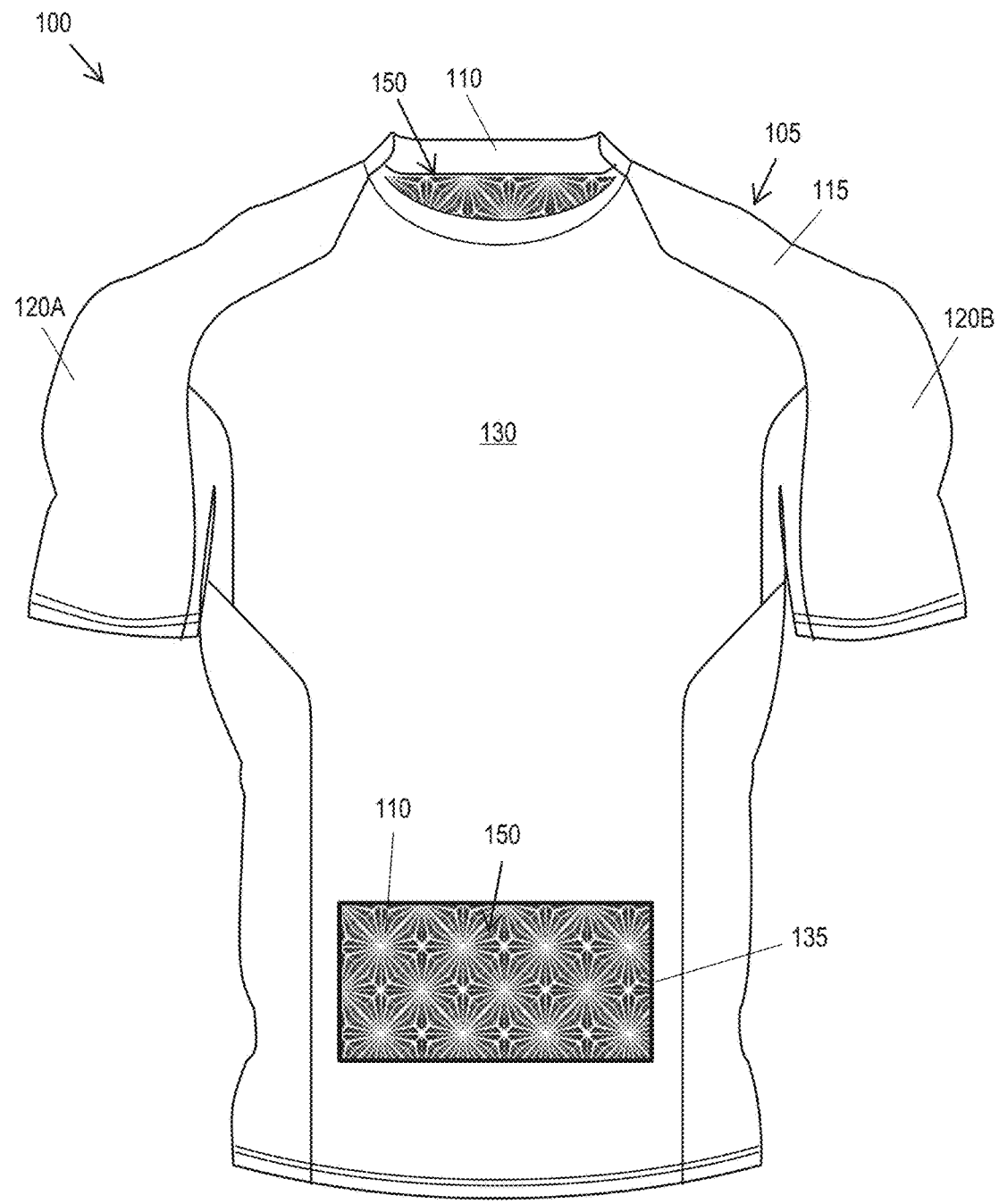
FIG. 1 illustrates a front view in elevation of an article of apparel in accordance with an embodiment of the invention.

Referring to FIG. 1, in an embodiment, an article of apparel 100 includes a base textile or substrate 105 with an inner surface 110 that faces (contacts) the wearer and an outer surface 115 that faces away from the wearer. The substrate 105 is a fabric (e.g., a woven, knitted, or non-woven fabric) including natural and/or synthetic yarns. By way of example, the yarns may be formed of nylon, polyester, rayon, cotton, elastane, wool, silk, or a blend thereof. The substrate 105 can be treated with dyes, colorants, pigments, UV absorbers, plasticizers, lubricants, flame inhibitors, rheology agents, etc., either before or after application of the delivery layer. The substrate 105 may be constructed to have one or more desired properties such as air permeability, absorbance, moisture vapor transmission, and/or capillary action (to draw sweat away from the wearer), abrasion resistance, anti-static properties, anti-microbial activity, water repellence, flame repellence, hydrophilicity, hydrophobicity, wind resistance, UV protection, resiliency, stain resistance, wrinkle resistance, etc. In a preferred embodiment, the substrate 105 is breathable, possessing an air permeability of at least 50 cfm, preferably greater than 70 cfm. By way of example, the substrate may possess an air permeability of about 75 cfm—about 205 cfm.

The substrate 105 forms at least a portion of the article of apparel 100. The article of apparel includes, but is not limited to, athletic wear such as compression garments, shirts, shorts, pants, headwear (e.g., headbands), outerwear (e.g., jackets, hats, gloves), footwear (e.g., shoes, boots, slippers), sleepwear, and undergarments. In the embodiment of FIG. 1, the article of apparel is a compression shirt including arms 120A, 120B and a torso 130. In the figure, the shirt is provided with a cut-away section 135 to reveal the apparel inner surface 110.

A delivery layer 150 is disposed on the inner (wearer-contacting) surface 110 of the substrate 105. The delivery layer includes a bioresorbable material (also called a bioabsorbable material) and, in particular, a bioresorbable (bioabsorbable) alloy. In an embodiment, the alloy includes a primary alkaline earth metal, a secondary alkaline earth metal, and a transition or post-transition metal. The primary alkaline earth metal possesses the largest weight percent within the alloy. Preferably, the primary alkaline earth metal is magnesium. The secondary alkaline earth metal is an alkaline earth metal that is not selected as the primary alkaline earth metal. Thus, when the primary alkaline earth metal is magnesium, the secondary alkaline earth metal may include beryllium (Be), calcium (Ca), or strontium (Sr). In a preferred embodiment, the secondary alkaline earth metal is calcium, strontium, or a blend thereof. Calcium is an essential element for the human body and is non-toxic. Strontium is present in human bones and has been shown to promote osteoblast function and increase bone formation.

Calcium and strontium strengthen magnesium alloys while increasing their corrosion resistance.

The transition metal selected is preferably chemically similar to magnesium. In an embodiment, the transition metal is zinc (Zn). Zinc, already present in the human body, strengthens the magnesium alloy via precipitation strengthening. Thus, zinc is effective to slow the degradation of magnesium in solution. Other transition metals include cadmium (Cd) and manganese (Mn).

The amount of each element forming the bioabsorbable alloy is selected to provide a desired rate of dissolution. Accordingly, by controlling the elements and the corresponding coating for the delivery layer, the magnesium alloy can be designed with controllable degradation rates. Thus, the article of apparel is capable of supplying bioabsorbable metals to the wearer, even after repeated washings of the article of apparel.

In an embodiment, the bioresorbable material includes about 90 wt % to about 99 wt % primary alkaline earth metal (e.g., magnesium), about 0.1 wt % to about 3 wt % secondary alkaline earth metal (e.g., calcium or strontium); and about 0.1 wt % to about 6 wt % transition metal (e.g., zinc).

A binder is utilized to adhere the bioresorbable material to the substrate 105 (e.g., to the yarns/fibers forming the substrate). In an embodiment, a dissolvable polymer not absorbed in the body may be utilized. In a preferred embodiment, a bioabsorbable polymer is utilized. The bioabsorbable polymer may include natural polymers (i.e., polymers derived from natural sources) such as collagen and various polysaccharides such as cellulose. Synthetic bioabsorbable polymers include microbial polyesters, aliphatic polyesters (e.g., polylactide and polycaprolactone), polyester polyethers (e.g., polydioxanone), and polyamino acids (e.g., poly(glycolic acid) and poly(lactic acid)). Additionally polyvinyl alcohol or polyurethane may be utilized.

The binder and the alloy are combined to form a bioresorbable composition. In an embodiment, the bioresorbable composition 220 includes about 30-60 wt % alloy, 10-20 wt % binder, and about 20-60 wt % solvent (e.g., an aqueous solvent).

Figure 2:
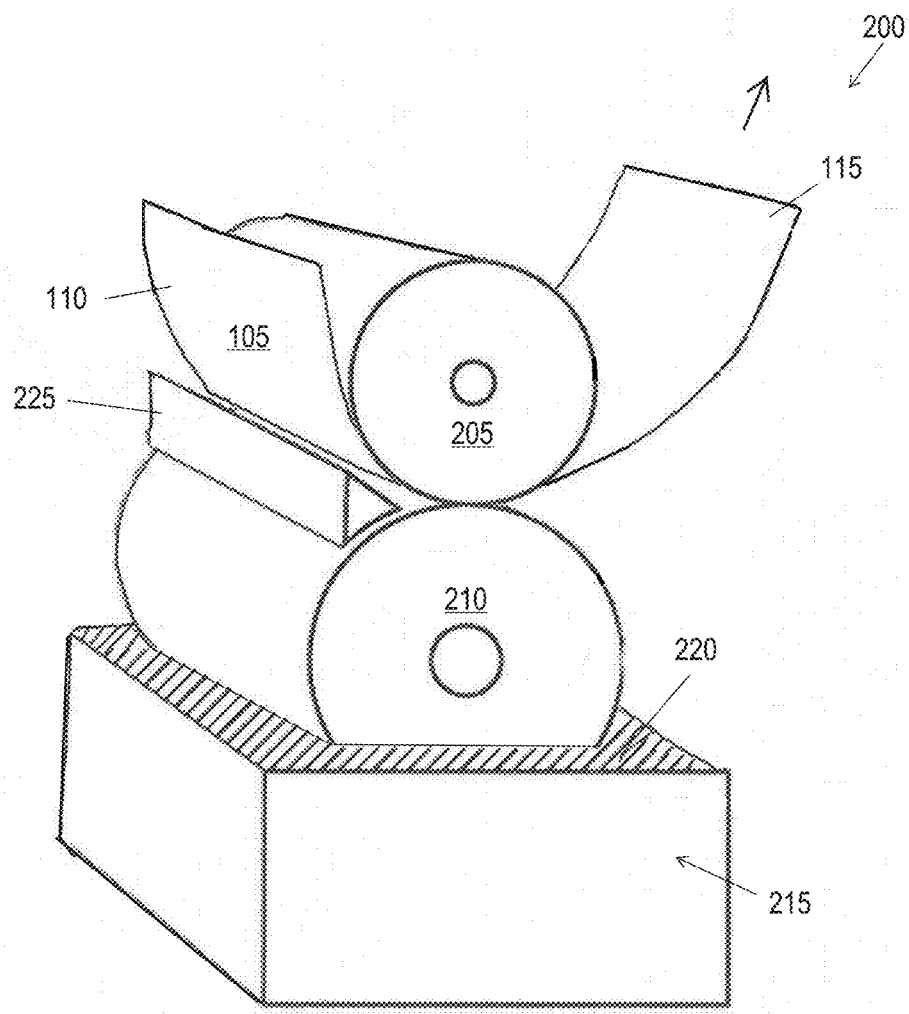
FIG. 2 illustrates a schematic of an apparatus for applying a coating to the substrate.

The delivery layer 150 is applied to the inner surface 110 of the substrate 105 in a manner that maintains the integrity of the components and preserves properties of the substrate. In an embodiment, the dynamic layer 150 is formed by applying the bioresorbable composition via a printing process. By way of example, the composition is transferred via a rotogravure apparatus 200. Referring to FIG. 2, the rotogravure apparatus 200 includes an impression roller 205, a gravure or etched cylinder 210, and a tank 215. The cylinder 210 is engraved/etched with recessed surface cells in a desired pattern (pattern not illustrated in FIG. 2). The tank 215 holds the bioresorbable composition 220. The apparatus 200 further includes a doctor blade 225 operable to remove excess composition from the cylinder 210.

In operation, as the cylinder 210 rotates, a portion of the cylinder becomes immersed in the bioresorbable composition 220 stored in the tank 215. The composition 220 coats the cylinder 210, becoming captured within the cells. The cylinder continues to rotate, moving the coated cylinder past the doctor blade 225, which removes excess composition 220 from the cylinder 210. The substrate 105 is directed between the impression roller 205 and the cylinder 210 such that the inner surface 110 of the substrate (e.g., what will be the wearer-facing side of the apparel) contacts the cylinder 210. Specifically, the impression roller 205 applies force to the substrate 105, pressing the substrate onto the cylinder 210, thereby ensuring even and maximum coverage of the thermal regulation composition 220. Surface tension forces pull the composition 220 out of the cells, transferring it to the substrate 105. Accordingly, the rotogravure apparatus 200 applies an initial or first pressure to the substrate 105 at an initial or first temperature (e.g., ambient temperature) to transfer the thermal regulation composition 220 to the substrate surface 115. Once the composition 220 is transferred, the coated substrate may pass through one or more heaters to evaporate the solvent, thereby drying the composition and forming the delivery layer 150. If a thicker membrane is desired, additional passes through the rotogravure apparatus 200 may be completed.

Figure 3:
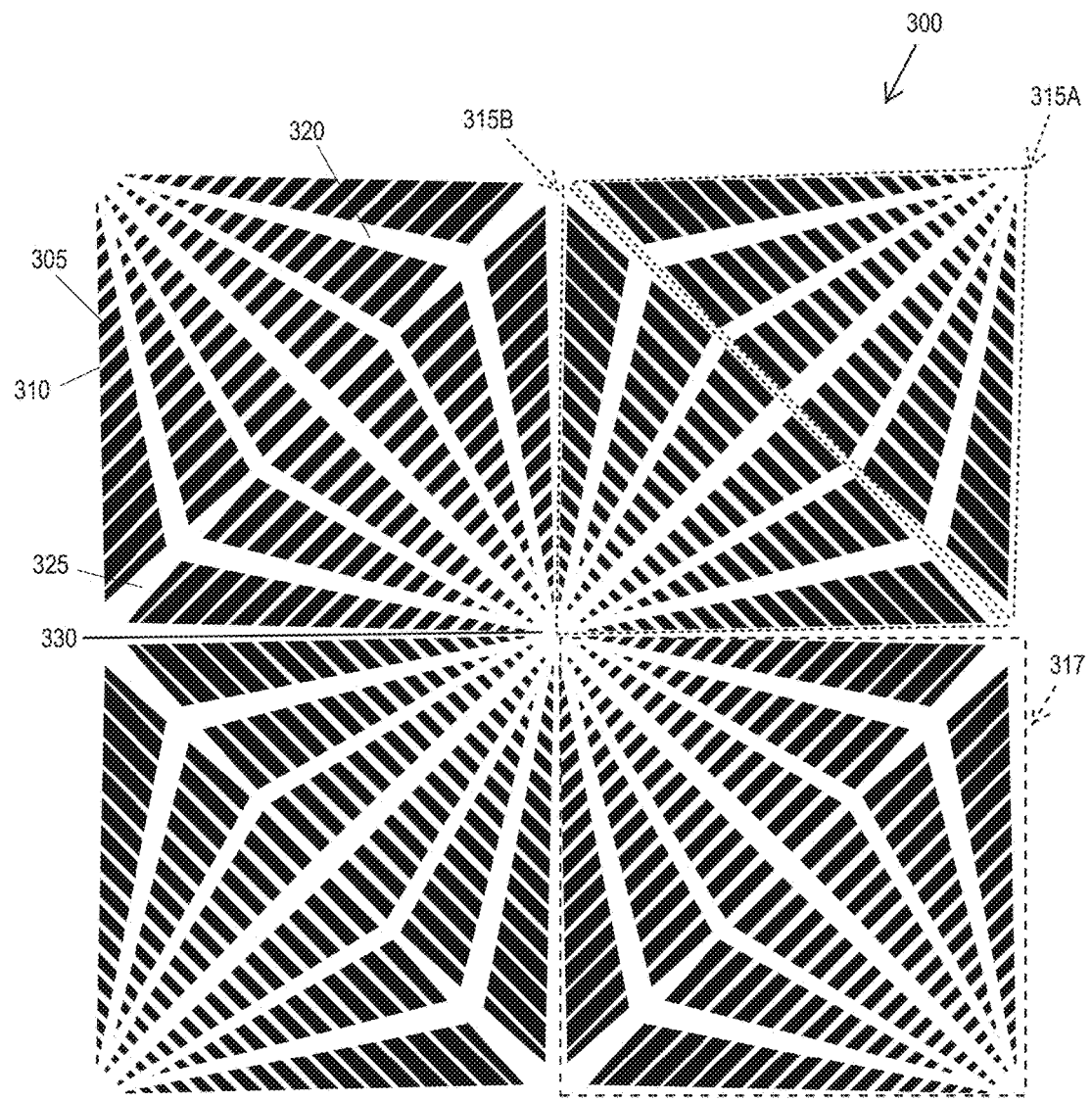
FIG. 3 illustrates an application pattern of the delivery layer in accordance with an embodiment of the invention.

The bioresorbable composition 220 may be applied to the substrate 105 in any pattern suitable for its described purpose. In an embodiment, the delivery layer 150 is applied in a repeating pattern of units. Referring to FIG. 3, each unit 300 includes generally linear elements 305 oriented in spaced relationship from each other, being separated by element channels 310 such that adjacent elements are oriented generally parallel to each other. The dimensions of each linear member 305 and channel 310 may be any suitable for its described purpose.

The linear members 305 are organized such that a discontinuous array of elements spans the substrate surface 110. In the illustrated embodiment, the linear members 305 are organized such that they cooperate to define a first or outer triangular section 315A and a second or inner triangular section 315B. The first triangular section 315A is a mirror image of the second triangular section 315B, and vice versa. The triangle sections 315A, 315B, in turn, cooperate to define a quadrant or substructure 317 of the unit 300. Each quadrant 317 is intersected by one or more (e.g., five) radial channels 320, as well as a segment channel 325 that separates the first triangle section 315A from the second triangle section 315B. The radial 320 and segment 325 channels may possess a wider transverse dimension than the element channels 310. The substructures 310, moreover, cooperate to define a central aperture 330 disposed the center of the structure 300.

Figure 4:
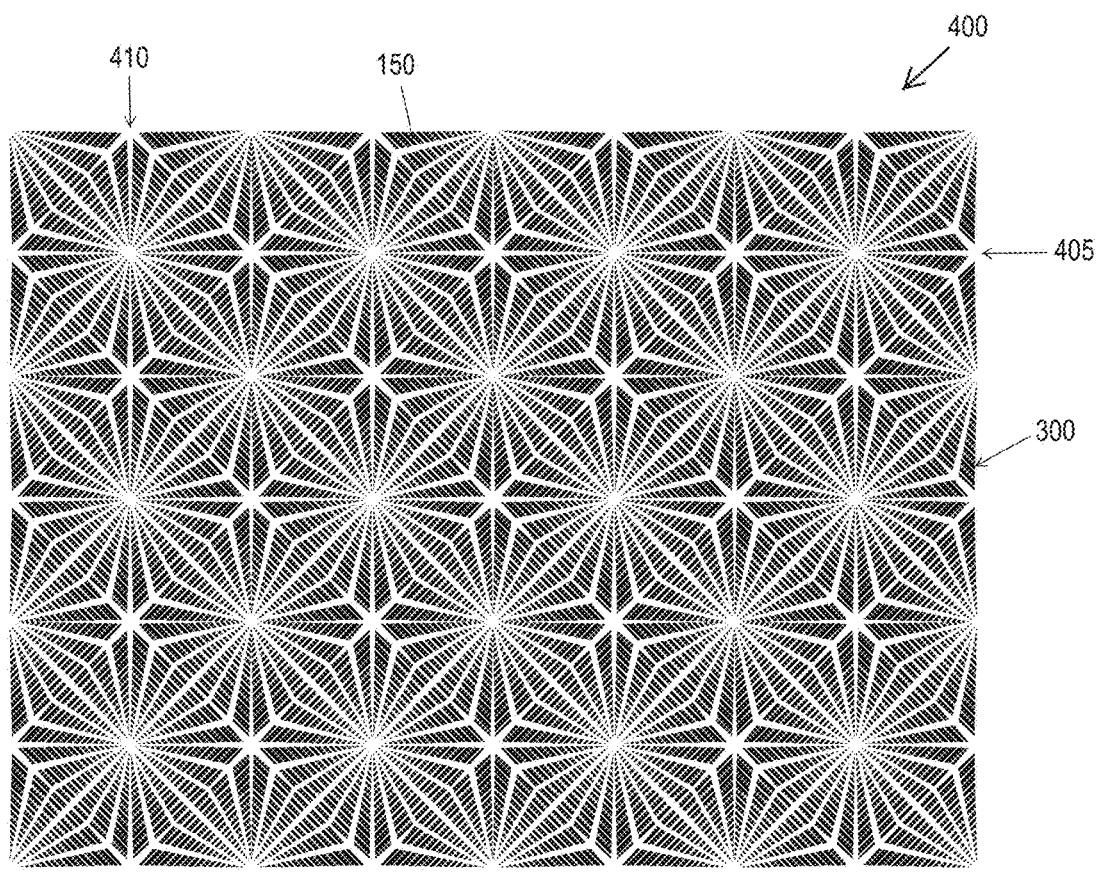
FIG. 4 illustrates the application pattern of FIG. 3, shown in an array.

Referring to FIG. 4, a plurality of units 300 are disposed adjacent each other form a pattern 400 on the substrate. Specifically, the units 300 are oriented in rows 405 and columns 410 along the substrate 110 such that a network of interconnecting channels is formed. With this configuration, the linear members 305 represent areas along the substrate including (covered by) the delivery layer 150. The channels 310, 320, 325 and apertures 330 in contrast, define areas free (e.g., substantially free) of the delivery layer 150. Each unit 300 of the pattern 400 may include a ratio of free area to treated area falling within predetermined values. By way of example, the ratio of free area to covered area may be approximately 3:1 (i.e., the treated area covers approximately 30% of the substrate surface 115).

After drying, the coated substrate 105 is processed to further integrate the delivery layer 150 into the fibers/yarns of the substrate. In an embodiment, the coated substrate 150 is subjected to a second pressure and temperature different from the temperature and pressure applied during the rotogravure process. In particular, the delivery layer 150 is subjected to a calendaring process in which the coated substrate is passed between a pair of heated rollers. The temperature of the rollers (and thus the temperature applied to a substrate surface (coated or non-coated)) may range from about 25° C. to about 55° C. Temperatures above this range cause puckering in the fabric (e.g., along the patterned areas). Temperatures below this range are generally insufficient to improve the hand of the fabric. In a preferred embodiment, the substrate 105 (e.g., the coated surface 115) is calendared at a temperature of approximately 30° C. The pressure applied to the substrate by the rollers ranges from about 30-70 lbs, with about 50 lbs being preferred.

Figure 5A:
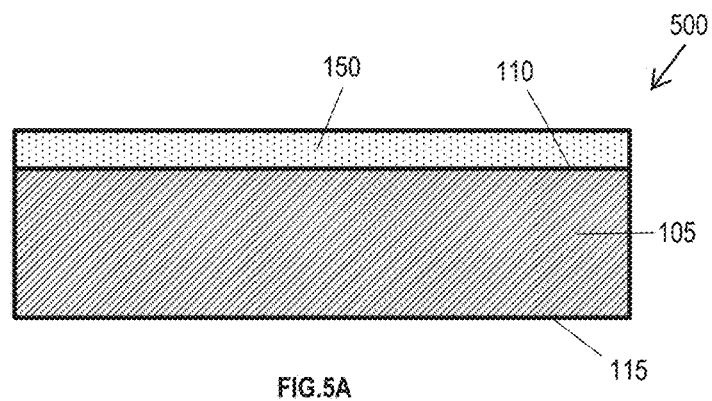
FIGS. 5A, 5B, and 5C illustrate the process wherein an apparatus applies heat and pressure to a coated substrate to integrate the delivery layer with the substrate.
Figure 5B:
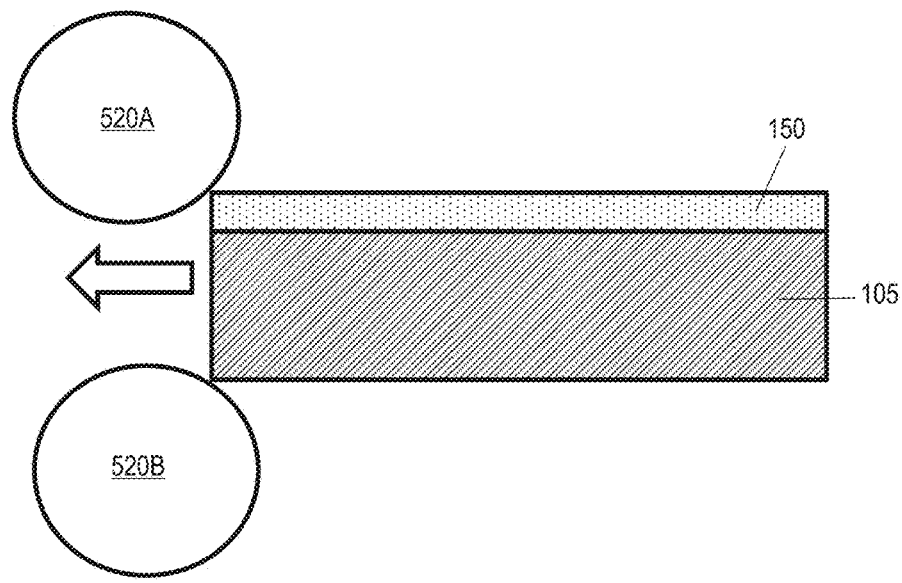
Figure 5C:
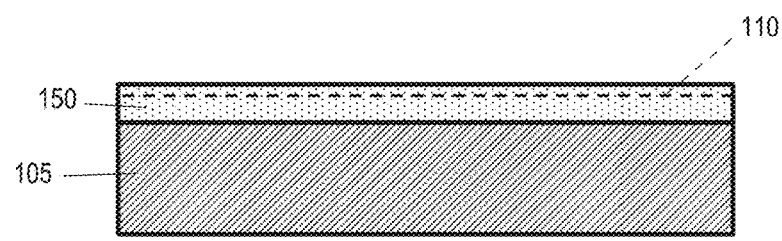

The above calendaring process not only improves the hand of the coated substrate, but also integrates the thermal regulation membrane 150 into the substrate 105. Referring to FIGS. 5A, 5B, and 5C, a coated substrate 500 includes the substrate 105 with the delivery layer 150 disposed on inner substrate surface 110 (while shown to be a continuous layer, it should be understood that the thermal regulation membrane may be discontinuous). The coated substrate 500 is drawn through the calendaring rollers 520A, 520B (FIG. 5B). As explained above, the rollers 520A, 520B apply heat and pressure to the substrate 105 and delivery layer 150, urging at least a portion of the membrane below the substrate surface 110. It is believed that the bioabsorable binder softens, permitting the delivery layer 150 to enter into the openings between the fibers and/or coat the fibers of the substrate 105. Alternatively, the heat and pressure may soften the substrate fibers, increasing the relative movement of the fibers, thereby creating openings in the textile that receive the delivery 150. Regardless, calendaring may result in yarns/fibers intersecting (e.g., protruding from) the delivery layer 150 and/or may result in the membrane coating/enveloping individual fibers along (e.g., below) the interface 110. As shown (FIG. 5C), after calendaring, the delivery layer 150 is pressed into the substrate 105 (beyond initial substrate surface 515), becoming integrated therewith.

Figure 6:
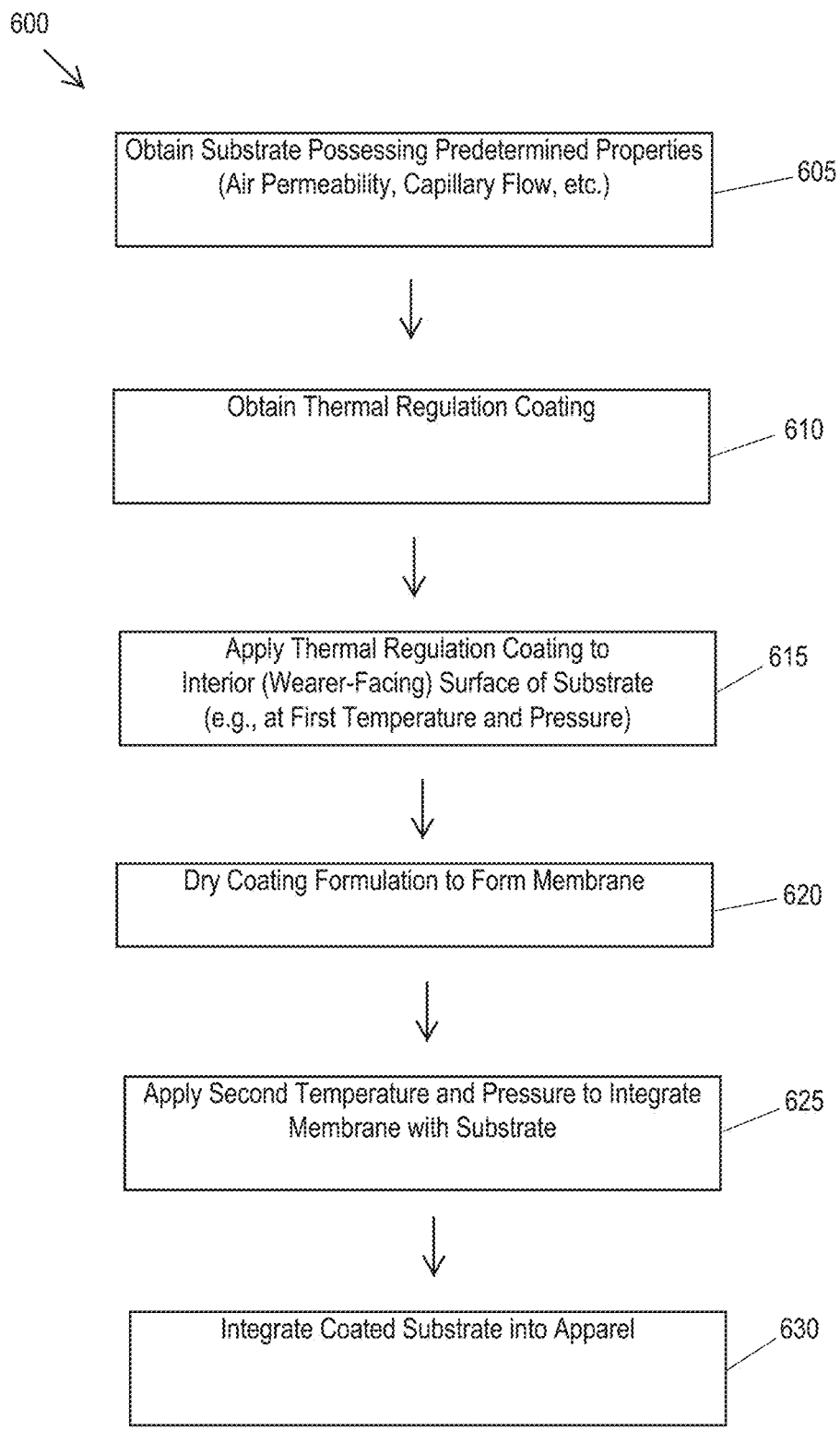
FIG. 6 illustrates a flow diagram of the process of forming the article of apparel.

The process of forming the article of apparel is explained with reference to FIG. 6. The process 600 begins at Step 605, with the substrate 105 being obtained. As explained above, the substrate 105 may be woven, non-woven, or knitted, and may possess predetermined properties falling within specified ranges (air permeability, fluid movement, etc.). By way of example, the substrate 105 is a four-way stretch fabric including polyester and elastane fibers. In Step 610, the bioresorbable coating is obtained.

In Step 615, the bioresorbable composition 220 is applied to the surface 110 (the wearer-contacting surface) of the substrate 105 at a first temperature and pressure in the manner explained above (via rotogravure). Once applied, at Step 620, the bioresorbable coating 220 is dried (e.g., via heating), thereby forming the delivery layer 150. Optionally, in step 625, the substrate 105 is processed at a second temperature and pressure. In particular, the coated substrate is calendared as explained above (roller temperature 30° C. at 50 lbs pressure and roll speed of 350 rpm). Finally, the coated and calendared substrate 105 may be integrated into an article of apparel in Step 630. By way of example, the substrate may be treated like conventional fabric, being cut and sewn to form a desired garment.

Figure 7A:
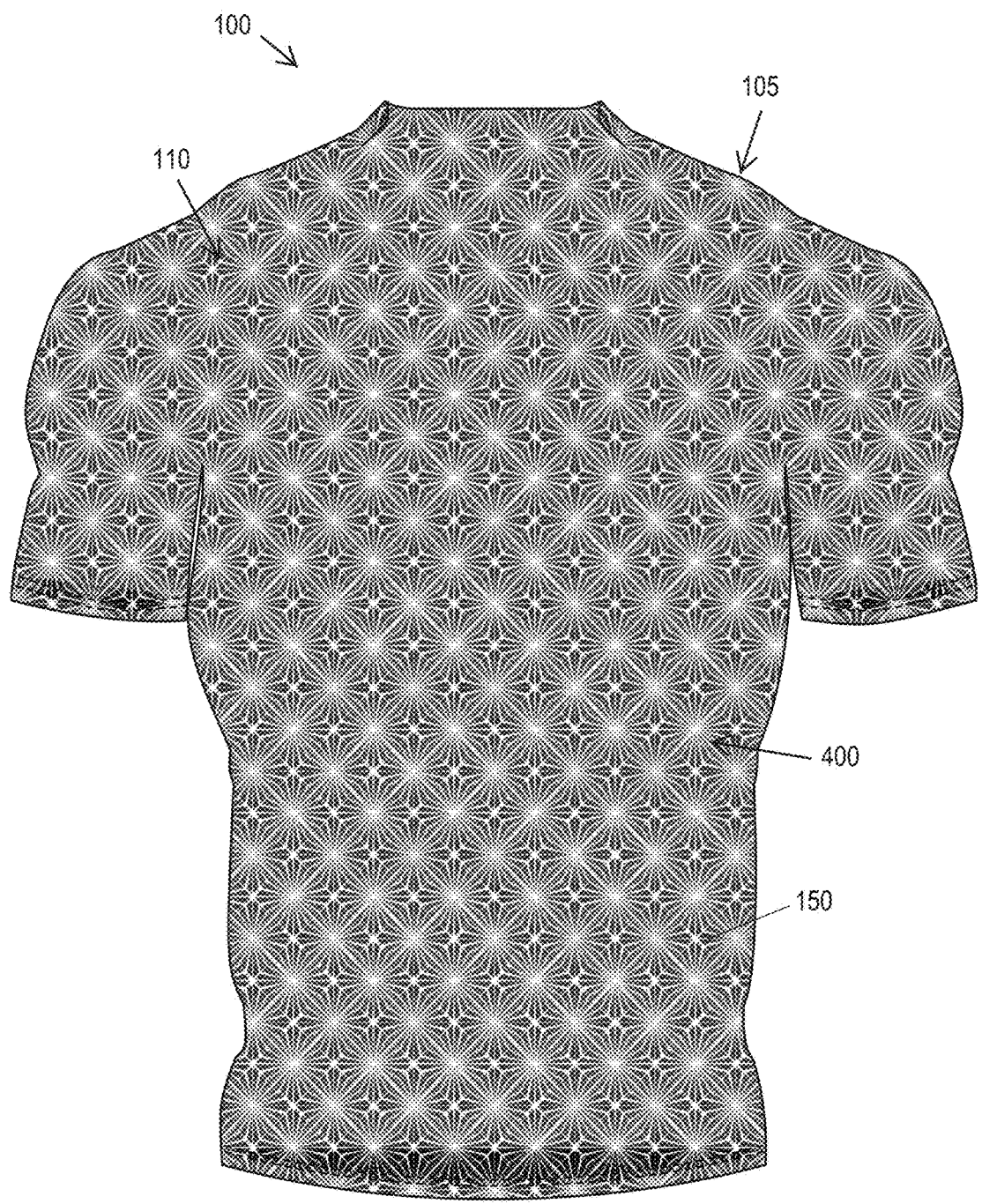
FIGS. 7A and 7B illustrate the application pattern of FIG. 4 applied to the interior surface of an article of apparel, with the patterns shown in a smaller (FIG. 7A) and larger (FIG. 7B) scale.
Figure 7B:
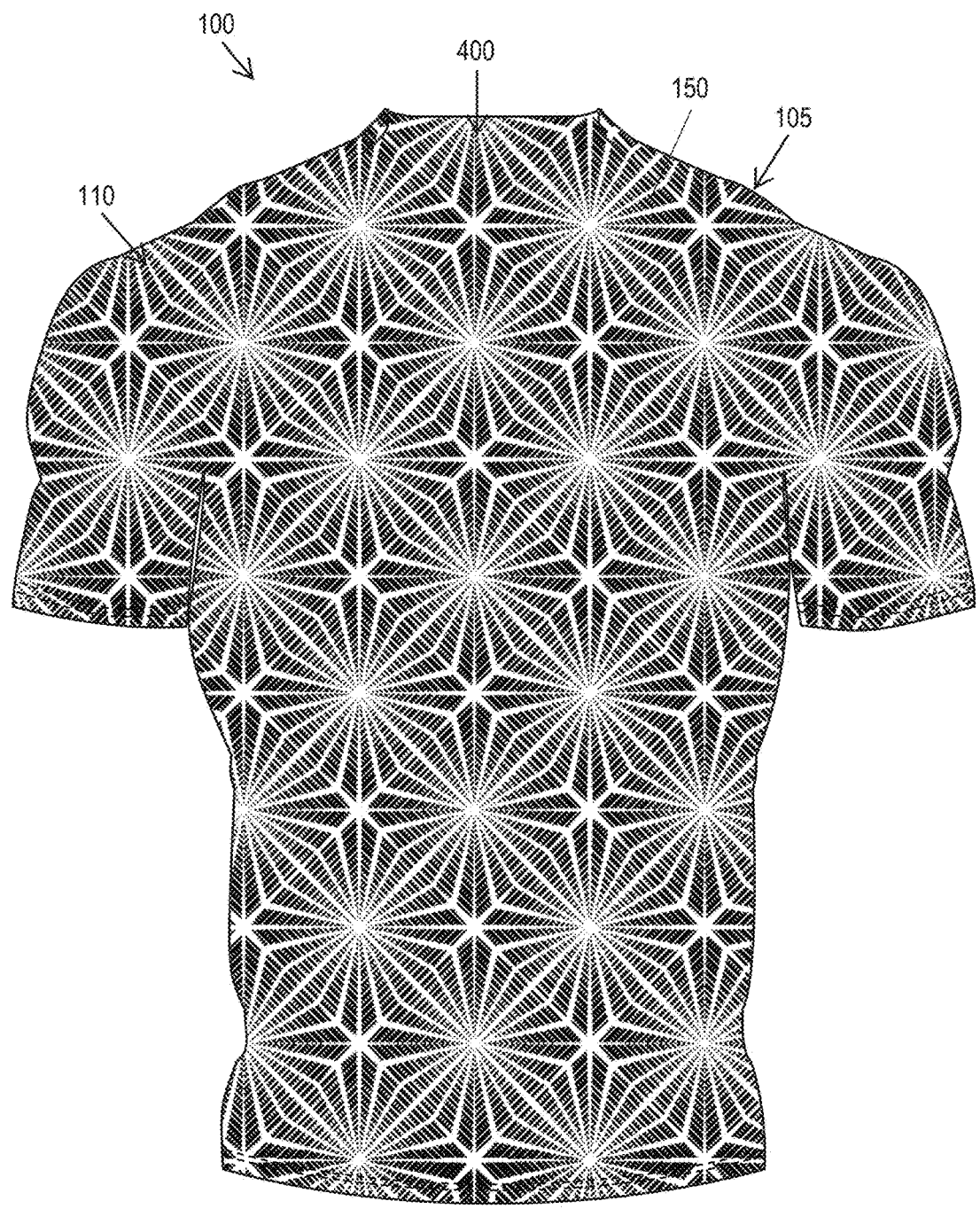

Referring to FIG. 7, the substrate 105 may form a compression shirt. The pattern 400 may be modified to provide the desired level of coverage. For example, the scale and/or density of the pattern may be modified. The embodiment of FIG. 7A possesses a high density pattern, which covers more surface area of the substrate than the low density pattern of FIG. 7B. As explained above, the desired level of coverage is up to about 30% of the surface area of the substrate 105. That is, when the delivery layer 150 is applied to the substrate 105, the surface area of the substrate surface 110 covered by the delivery layer is approximately 30% or less.

In a preferred embodiment, the delivery layer is located to align with areas of the human body where absorption into the blood occurs easily. By way of example, the delivery layer is in registry with the neck, armpits, groin, along the spine, the collar, and the ventral side of the arms.

In an alternative embodiment, the substrate 105 may form a compression short, underwear, or leggings. The pattern 400 may be modified to provide the desired level of coverage. As described above, the scale and/or density of the pattern may be modified. Specifically, it is desirable to align the substrate with areas of the lower body that would benefit most from the therapeutic and preventive effects of the bioresorbable composition. Based on the fundamental importance of the hips, groin, and legs to movement during athletic activity, the buttocks, groin, quadriceps, hamstrings, and calves are crucial areas to target, and covering said areas is a critical step to delivering the bioresorbable composition.

The resulting delivery layer 150 is effective to deliver bioabsorbable metals to a wearer. While not being bound to theory, it is believed that the delivery layer 150 dissolves in two stages, reacting to the environment (the interface between the article of apparel 100 and the skin of the wearer). In the first stage, it is believed the moisture dissipation agent is active immediately upon placement onto a user. In the presence of the moisture from the water concentration of human skin, at body temperature (e.g. 85 F to 98 F), the magnesium alloy degrades to form magnesium hydroxide. Since the delivery layer is in contact with the skin, the magnesium hydroxide is transferred to the skin of the wearer and is topically absorbed to a moderate degree.

Additionally, when the temperature of the wearer increases, the body's evaporative cooling response will activate, causing the body to perspire. Once exuded, the perspiration (water) will contact the delivery layer 150. Accordingly, the delivery layer degrades and, in the presence of a chloride concentration (NaCl, generated, e.g., via perspiration), the alloy will experience a new reaction and form magnesium chloride. Magnesium chloride is topically absorbed to a higher degree because it is more bioavailable than magnesium hydroxide.

In another embodiment, the bioresorbable alloy is provided in the fibers forming the textile, omitting the need for a delivery layer 150. For example, the fiber may be spun with the alloy, or the fiber may be treated with a composition containing the alloy, coating the fibers with the alloy. In still other embodiments, filaments formed via extrusion may include the fiber material combined with the alloy. An exemplary manner of forming such a metallized fiber is provided in US20140227504, the disclosure of which is incorporated by reference in its entirety. In still other embodiments, fine wires composed of the alloy may be incorporated into the woven or knit structure of the garment in the key absorption areas described in 0031 and 0032. These wires are available from nanoMAG (Livonia, Mich.) in 0.3 mm and 1.1 mm diameters sizes.

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. It is to be understood that terms such as "top", "bottom", "front", "rear", "side", "height", "length", "width", "upper", "lower", "interior", "exterior", and the like as may be used herein, merely describe points of reference and do not limit the present invention to any particular orientation or configuration.

What is claimed is:

1. A method of forming an article of apparel, the method comprising:
   obtaining a textile substrate;
   applying a composition including a bioresorbable material including a therapeutically effective amount of magnesium or magnesium alloy to a surface of the textile substrate to form a coated textile substrate, wherein the composition includes about 30-60wt % magnesium (Mg) or magnesium alloy, 10-20wt % of a binder, and about 20-60wt % of an aqueous solvent;
   drying the coated textile substrate to form a delivery layer disposed on the surface of the textile substrate; and
   incorporating the substrate into an article of apparel with the bioresorbable on a surface of the apparel in contact with the wearer's skin when the apparel is worn.

2. The method according to claim 1, wherein the composition is applied via a rotogravure apparatus including an impression roller, a gravure or etched cylinder, and a tank.

3. The method according to claim 2, further comprising calendaring the textile substrate after application of the composition.

4. The method according to claim 3, wherein calendaring includes passing the substrate between a pair of heated rollers, the temperature of the rollers being with a range of from about 25° C. to about 55° C.

5. The method according to claim 4, wherein the composition is applied in a discontinuous pattern.

6. The method according to claim 5, wherein the discontinuous pattern is defined by linear members comprising areas covered by the composition and channels comprising areas free of the composition.

7. The method according to claim 6, wherein the ratio of free area to covered area is approximately 3:1.

8. The method according to claim 1, wherein the magnesium alloy includes magnesium and a secondary alkaline earth metal other than magnesium.

9. The method according to claim 8, wherein the secondary alkaline earth metal is selected from the group consisting of beryllium (Be), calcium (Ca), strontium (Sr), and combinations of one or more thereof.

10. The method according to claim 8, wherein the bioresorbable material includes about 90wt % to about 99wt % magnesium (Mg), about 0.1wt % to about 3wt % secondary alkaline earth metal; and about 0.1wt % to about 6 wt % of a transition metal.

11. The method according to claim 10, wherein the transition metal is selected from the group consisting of zinc (Zn), cadmium (Cd) and manganese (Mn).

12. The method according to claim 10, wherein the secondary alkaline earth metal is selected from the group consisting of beryllium (Be), calcium (Ca), strontium (Sr), and combinations of one or more thereof.

* * * * *